US006796947B2

(12) United States Patent
Watt et al.

(10) Patent No.: US 6,796,947 B2
(45) Date of Patent: Sep. 28, 2004

(54) METHOD FOR EVALUATING VESTIBULAR RESPONSE

(75) Inventors: Douglas Watt, Montreal (CA); Luc Lefebvre, Montreal (CA)

(73) Assignee: Canadian Space Agency, St. Hubert (CA)

( * ) Notice: Subject to any disclaimer, the term of this patent is extended or adjusted under 35 U.S.C. 154(b) by 177 days.

(21) Appl. No.: 10/048,913
(22) PCT Filed: Jun. 18, 2001
(86) PCT No.: PCT/CA01/00894
§ 371 (c)(1),
(2), (4) Date: May 10, 2002
(87) PCT Pub. No.: WO01/97684
PCT Pub. Date: Dec. 27, 2001

(65) Prior Publication Data
US 2002/0151818 A1 Oct. 17, 2002

Related U.S. Application Data
(60) Provisional application No. 60/212,641, filed on Jun. 19, 2000.

(51) Int. Cl.[7] .................................................. A61B 5/00
(52) U.S. Cl. ........................................ 600/552; 600/595
(58) Field of Search ............................... 600/552, 553, 600/558, 587, 595

(56) References Cited

U.S. PATENT DOCUMENTS 4,474,186 A * 10/1984 Ledley et al. ............... 600/546
5,942,954 A * 8/1999 Galiana et al. ............. 600/546

OTHER PUBLICATIONS

Ivanenko, YP et al., "Effect of gaze on postural responses to neck proprioceptive and vestibular stimulation in humans," Journal of Physiology, vol. 519.1, pp. 301–314, 1999.*

* cited by examiner

Primary Examiner—Eric F. Winakur
(74) Attorney, Agent, or Firm—Marks & Clerk

(57) ABSTRACT

A method is disclosed for evaluating the vestibular function in a human subject. The subject is constrained in a substantially erect position so that the head moves in unison with the rest of the body. A controlled stimulus in the form of a sudden angular acceleration is imparted to the body, and the subject's ocular response to the controlled stimulus is measured. The vestibular function is evaluated from the ocular response and the angular velocity of the head.

32 Claims, 5 Drawing Sheets

METHOD FOR EVALUATING VESTIBULAR RESPONSE

CROSS REFERENCE TO RELATED APPLICATION

This application claims the benefit of under 35 USC 119(e) of U.S. provisional application Ser. No. 60/212,641 filed Jun. 19, 2000.

BACKGROUND OF THE INVENTION

1. Field of the Invention

This invention relates to the field of vestibular testing, more particularly to a method and apparatus for the clinical evaluation of the balance organs of the inner ear.

2. Description of Related Art

Dizziness is one of the most common clinical complaints around the world. Functional testing of the vestibular system (the balance organs of the inner ear) is often necessary for correct diagnosis and treatment, but accurate tests are costly and complex.

It has been reported that dizziness is the most common motive for consultation of a physician in patients over seventy five years of age. While in some cases the symptoms are typical and a cause is easily established, in many other cases a specific diagnosis depends on precise functional testing, particularly of the vestibular system. At the present time, this testing is very costly, and requires highly trained operators to interpret the results.

The inner ear consists of two parts, the cochlea that transduces sound waves and allows us to hear, and the vestibular labyrinth that senses movement and generates reflexes to stabilize our eyes, heads and bodies. Usually, acute damage to the labyrinth will produce false sensations of movement, often called vertigo or dizziness, as well as gaze and postural instability and motion sickness. These symptoms tend to become increasingly vague, however, as compensation develops. As a result, it can be difficult to distinguish between vestibular and other problems of a quite different nature. Of course, prognosis and treatment depend heavily on a correct diagnosis.

One common method of testing the vestibular system consists of squirting warm or cool water into each ear canal and monitoring the resulting "caloric nystagmus". These involuntary eye movements result largely but not exclusively from thermally-induced convection currents in endolymph, particularly in the horizontal canal. The results of caloric testing are combined with separate assessments of the eye movement control system and of eye movements that result from changes in the patient's position. This is usually referred to as the electronystagmogram (ENG) test battery. While helpful in some cases, it often provides equivocal data in patients with mild symptoms, and these are precisely the ones for which an objective test is necessary.

The only way to apply a selective and controlled stimulus to the vestibular system is to expose the patient to physical movement. Furthermore, this movement must be of a sort that makes it impossible for predictive or other compensatory mechanisms to hide deficits in vestibular function. Normally, this means fast, because the neural circuits underlying compensation are more complex and hence slower than the very simple pathways used by vestibular reflexes. However, sudden movements require powerful machines, such as high-torque servo-controlled rotators, as in rotary chair apparatus. A safe, man-rated version of these devices can be costly, require recurrent inspections, maintenance and repairs. As a result, such devices and the sophisticated vestibular testing they make possible have been limited to a relatively few university teaching hospitals.

Australian researchers Ian Curthoys and Michael Halmagyi (Halmagyi, G. M., Curthoys, I. S., Cremer, P. D., Henderson, C. J., Todd, M. J., Staples, M. J. and D'Cruz, D. M. The human horizontal vestibulo-ocular reflex in response to high-acceleration stimulation before and after unilateral vestibular neurectomy. Exp. Brain Res. 81: 479–490, 1990.) have demonstrated a far simpler technique that measures eye movements during the first 100 msec of an unpredictable, passive horizontal head rotation (peak head displacement 20°, peak head velocity 200–300°/sec, peak head acceleration 2000–4000°/sec$^2$). When eye velocity is plotted as a function of head velocity in patients with an unilateral loss of vestibular function, eye responses during rotations toward the intact side are found to be close to normal but the responses are found to be markedly decreased when the rotation is toward the lesioned side. Most significantly, this deficit appears to be permanent, implying that it cannot be hidden by compensatory mechanisms.

This work is a significant step towards a simple and practical clinical test of human vestibular function, but it has one serious drawback. To reach significant head angular velocities in less than 100 msec, large head angular accelerations are necessary. These are achieved by the examiner abruptly and unpredictably rotating the patient's head only. This movement would inevitably be opposed by involuntary stretch reflexes and could lead to severe consequences in the presence of undetected cervical spinal pathology. While similar, rapid head rotations can be produced voluntarily, such a method would suffer badly from predictability of the stimulus. As well, not everyone can perform the maneuver in an acceptable fashion.

There is a need to provide a simple, effective and inexpensive technology that would allow diagnostic testing in many additional hospitals, clinics and offices.

SUMMARY OF THE INVENTION

According to the present invention there is provided a method of evaluating the vestibular function in a human subject, wherein the human subject is constrained in a substantially erect position so that the head moves in unison with the rest of the body, a controlled stimulus in the form of a sudden angular acceleration is imparted to the body, and the subject's ocular response to the controlled stimulus is measured.

Typically, the subject is placed in a pivotable mechanism, such as a frame that can pivot essentially about the vertical axis or another axis. The subject is essentially erect within the frame and is stabilized in a vertical standing position, or in a horizontal position, or in an inclined position relative to the vertical. The subject's head is substantially immobile relative to the torso or the rest of the body. The head may be immobilized by various means, such as a clamp consisting of a pair of brackets.

After the initial acceleration the subject is preferably brought to a rapid standstill with the aid of a fluid damping mechanism that exploits the fact that during an initial period of laminar flow, the resistance to motion of a body moving in a fluid is very low, and then with the onset of turbulent flow, this resistance suddenly increases.

The subject's response to this controlled stimulus is preferably measured using electro-oculography (EOG), which is the recording of electrical signals produced by eye movement. The stimulus is recorded using angular velocity transducers. Surface electrodes used in conjunction with a forehead-mounted ring and adjustable connectors are a convenient way of performing electro-oculographic recording. Angular velocity transducers are preferably secured in place with a head adaptor allowing for the precise measurement of the angular speed of the head without slip.

Vestibular function can be assessed using eye versus head velocity data. Eye velocity is derived from eye position data. Further decision analysis can be based on eye velocity versus head velocity curves.

An alternative approach would be to use a man-powered rotator, including a seat, a footrest and a means of securing the subject's upper body and head to the chair. Unfortunately, such a device has great difficulty achieving adequate angular acceleration. Fully half of one's body mass is located in the legs. In the sitting position, this is distributed far from the axis of rotation, greatly increasing angular inertia. Such a human powered head rotator type could not reach the angular accelerations necessary for the method of Curthoys and Halmagyi. The applicants have found surprisingly that the method of the invention achieves the necessary angular rotation in a simple and effective manner.

In another aspect the invention provides an apparatus for evaluating vestibular function in a human subject comprising a frame for supporting the human subject in a substantially erect position with the head constrained so that it moves in unison with the rest of the body, the frame being rotatable about a longitudinal axis of the subject, an arrangement for measuring ocular response to a controlled stimulus in the form of a sudden angular acceleration imparted to the frame, at least one sensor for measuring the angular velocity of the subject's head, and a processing unit for deriving the vestibular function from the subject's ocular response and the angular velocity.

BRIEF DESCRIPTION OF THE DRAWINGS

The invention will now be described in more detail, by way of example, only with reference to the accompanying drawings, in which.

DETAILED DESCRIPTION OF THE INVENTION

Figure 1:
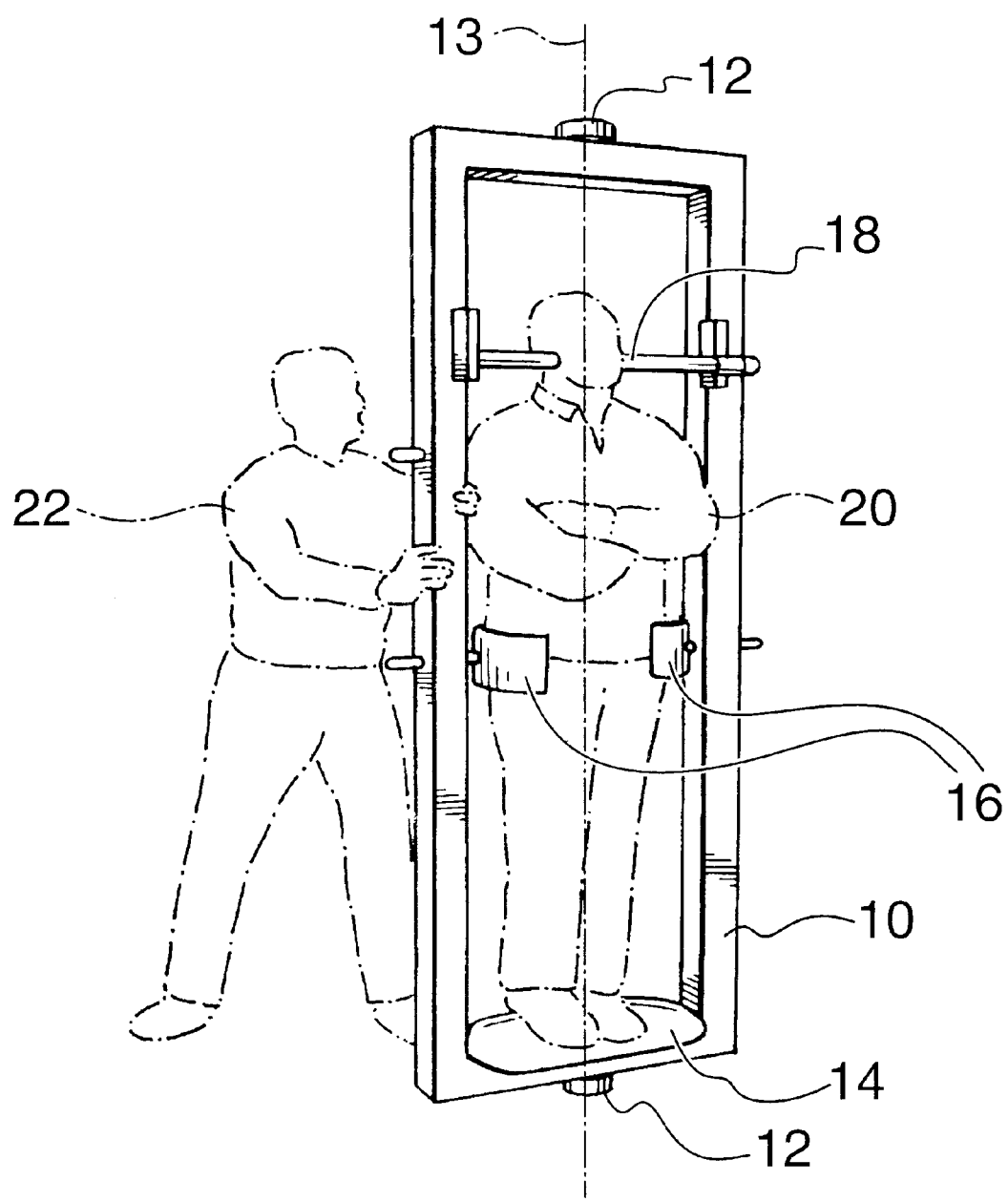
FIG. 1 is an illustration of an experimental set-up of a vestibular response evaluation apparatus in which the subject stands close to the center of a rotatable frame.
Figure 2:
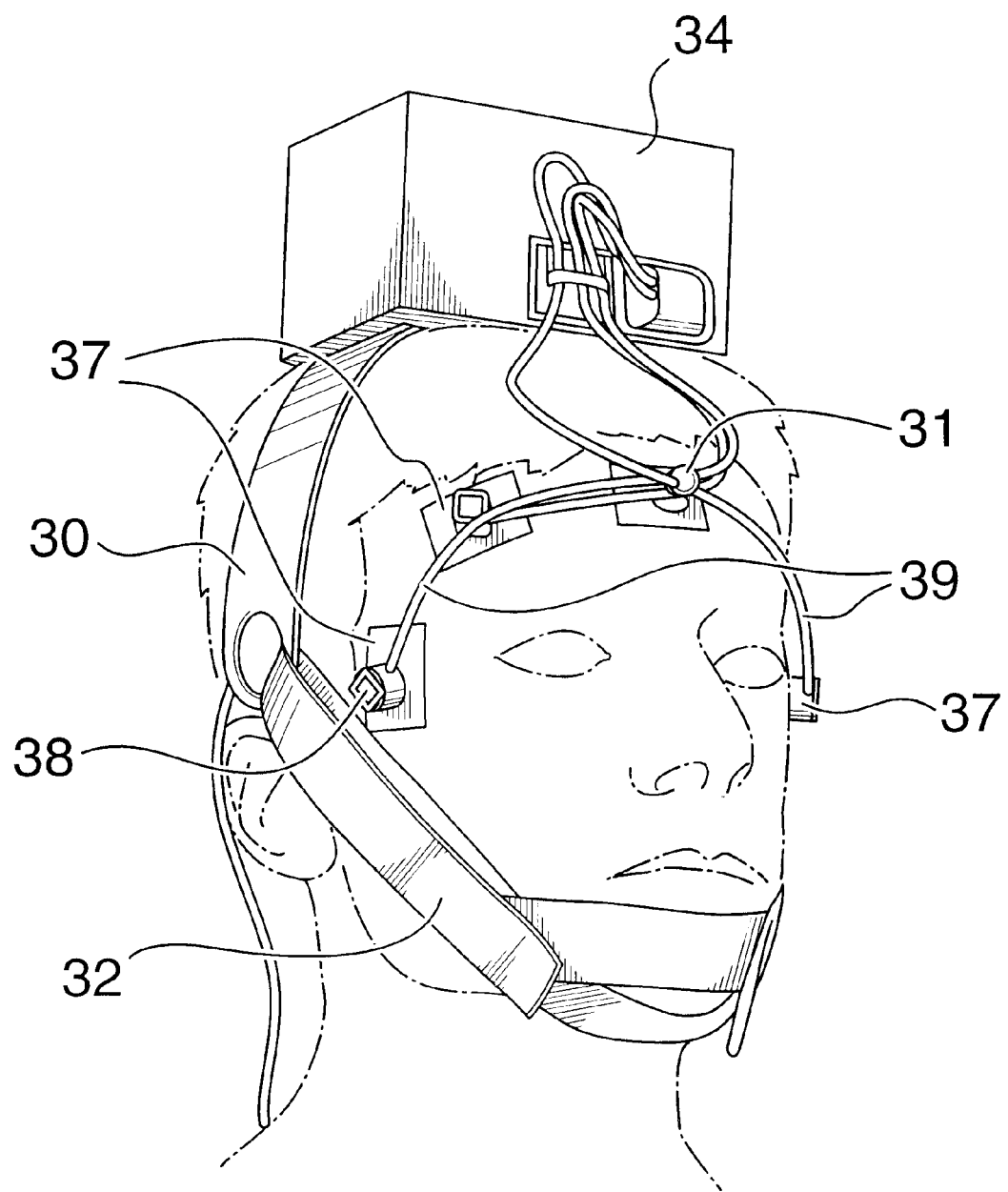
FIG. 2 is a schematic block diagram of a method for stimulating the vestibular system of the subject in vertical axis position and measuring the vestibular and ocular response.
Figure 3:
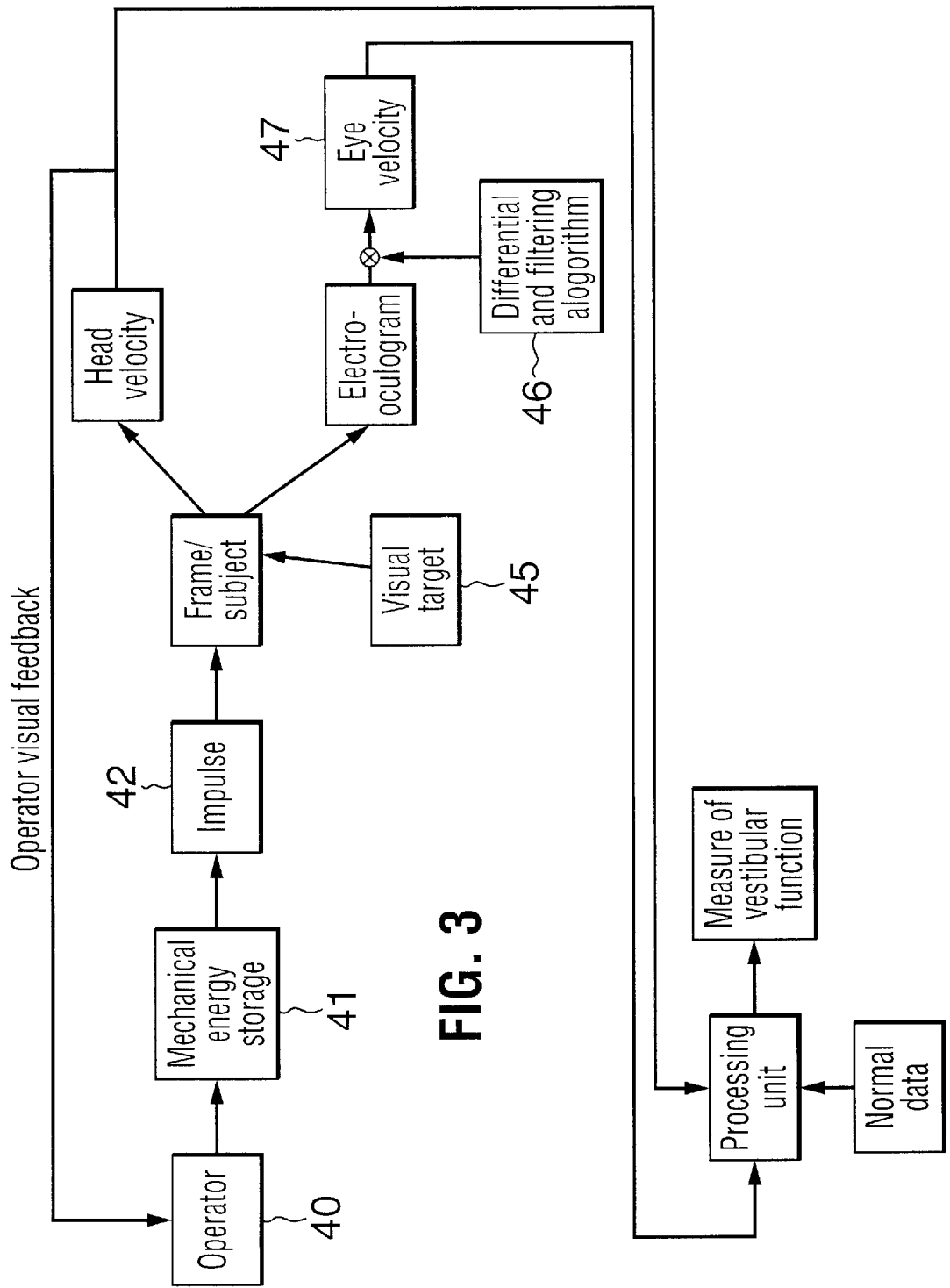
FIG. 3 illustrates hardware including a forehead mounted ring, adjustable electrode connectors, and a head adaptor capable of measuring eye and head movements.

FIG. 1 shows an apparatus for evaluating the vestibular response of a human subject. The apparatus comprises a rectangular frame 10 having upper and lower bearings 12 arranged such that the frame is rotatable about symmetrical vertical axis 13. In use, a human subject 20 stands in the erect position on platform 14 such that the axis of rotation 13 extends along the longitudinal axis and is constrained at the hips by brackets 16 and at the head by brackets 18. In use, an operator 22 imparts a sudden rotational movement to the frame 10. As a result the subject rotates about the axis with the head and torso rotating together in unison.

In the illustrated embodiment, the frame is rotatable about the vertical axis. It will be understood the frame could be mounted so as to allow rotation about different axes so long as they pass through the longitudinal axis of the subject. For example, the subject could be rotated in the horizontal position with suitable supporting harnesses.

The subject wears a harness 30 with chin strap 32 supporting an electronics package 34 on the head. The electronics package, which contains an amplifier and three mutually perpendicular angular velocity sensors, is connected to ocular electrodes for recording electrical signals resulting from eye movement of the subject. The ocular electrodes 37 are conventional stick-on electrodes that are mounted to the side and above the eye. The equipment is capable of measuring eye and head movements with high angular and temporal resolution.

The electrodes 37 are connected by box-shaped connectors 38 to EOG electrode leads 39 extending into the electronics package 34. The electrode leads are stabilized with a stabilizing ring 31 attached to the forehead of the subject. The stabilizing ring 31, which can conveniently be a redundant electrode that is not used for signal collection, reduces signal artifacts that result from the relative movement of the connectors 38 and the head of the subject. In this case the electrode can be stuck on the forehead and the same manner as the active electrodes 38. The box-shaped electrode connectors 38 are adjustable so as to improve the quality of recordings by minimizing motion artifacts caused by mechanical stress on the electrodes.

As illustrated in the FIG. 1, in order to evaluate vestibular response, the operator at step 40 imparts a sudden angular acceleration to a subject supported in a standing position. This can be by done manually or through a controlled mechanical device that includes a mechanical energy storage device 41, such as a flywheel, and an impulse unit 42 for suddenly releasing the stored energy as rotational energy driving the frame 18. The subject is provided with a visual target 45 on which to gaze.

The head velocity and eye response to this controlled stimulus are measured using three mutually perpendicular angular velocity transducers and an electro-oculogram, which can be included in the electronics package 34 or mounted externally. In this case, it can communicate with the electronics package by a wireless link. Electrooculography is a well-known technique to persons skilled in the art.

The electrooculographic data (EOG) are processed through various differentiation and filtering algorithms 46 to derive eye velocity 47.

Software analysis provides decision analysis based on eye versus head velocity. Comparison with normal subject data are used to interpret this analysis. The interactive software can also provide a feedback reference to the operator. A measure of the vestibular function is then derived.

In the wood prototype apparatus shown in FIG. 1, the machine was capable of reaching angular velocities of 175°/sec and displacements of 7° within 100 msec while rotating the entire subject as a rigid body. These values are only slightly lower than those achieved when only the head is rotated. Furthermore, only moderate effort is necessary on the part of the operator to apply the impulse manually and the ride is very benign from the subject's point of view.

The use of digital signal processing techniques on the EOG data both before and after differentiation yields exceptionally clean eye velocity information. This also yields uniform and automated saccade and blink extraction.

Figure 4:
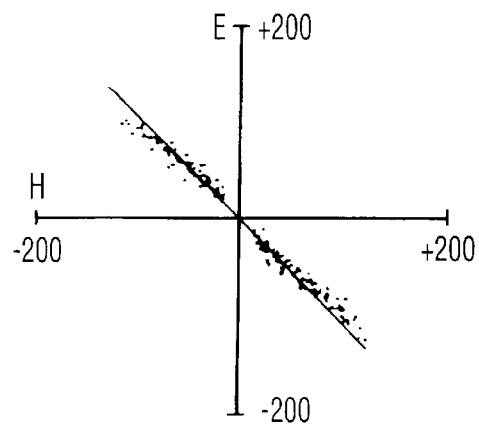
FIG. 4 shows results obtained from a subject having normal sensitivity.
Figure 5:
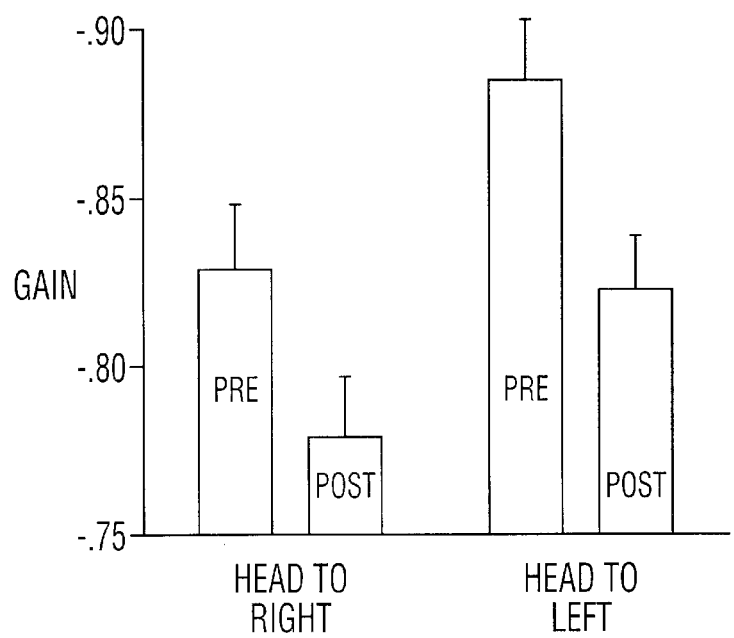
FIG. 5 shows the results obtained from a subject after an acute change in sensitivity.
Figure 6:
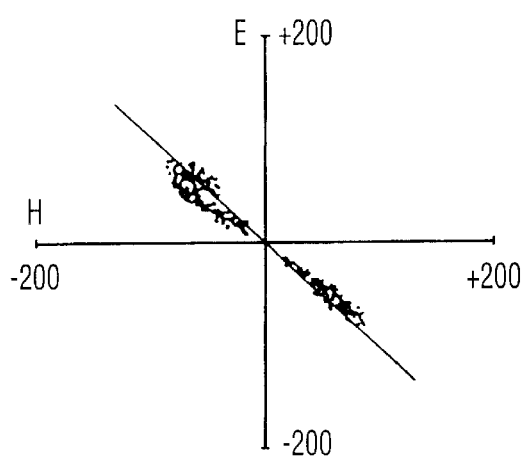
FIG. 6 shows the results obtained from a subject after a chronic change in sensitivity.

Analysis:

The description of the data analysis and decision processes of the method is described in the preliminary results analysis shown in FIGS. 4, 5, and 6 for the vestibular conditions of typical subjects.

In a first experiment shown in FIG. 4, a normal subject was exposed to 50 rotations in alternating directions. Eye position was converted to eye velocity and the latter was plotted as a function of head velocity on a sample by sample basis. This normal subject was able to keep his eye on the target without any difficulty. Points falling on the diagonal line indicate perfect tracking. The recording equipment and analytical techniques produced little data scatter, making it possible to detect changes of the order of 5%.

In a second experiment, an acute change condition is characterized, as illustrated in FIG. 5. A method known as "torso rotation" is used to induce a small, temporary and bilateral reduction in vestibular sensitivity in a subject. The subject was tested before and immediately after the procedure. In this case, linear regression (best fit) lines were calculated separately for the points in the upper left and lower right quadrants to provide an objective measure of the gain (sensitivity) of the system for each direction of rotation. These results are summarized in FIG. 5, including the value of each measured slope and its standard error. Responses to head rotation to the right were reduced by 6% and those caused by rotation to the left decreased by 7%. Both of these changes were statistically significant. A pre-existing directional asymmetry was also preserved after "torso rotation".

Finally, three patients with long-standing, unilateral loss of vestibular function were tested to determine if the method could detect and lateralize the lesions despite compensation developing over a period of one to two years. FIG. 6 indicates that it can. During sudden rotations to the right (lower right quadrant), the first subject performed well if not perfectly. However, rotations to the left (upper left quadrant) produced eye movements that were quite slow initially followed by a sudden attempt to "catch up". This produced a distinctive, hook-shaped response that could be seen in all three patients when they were rotated towards the side of their lesions.

Figure 7:
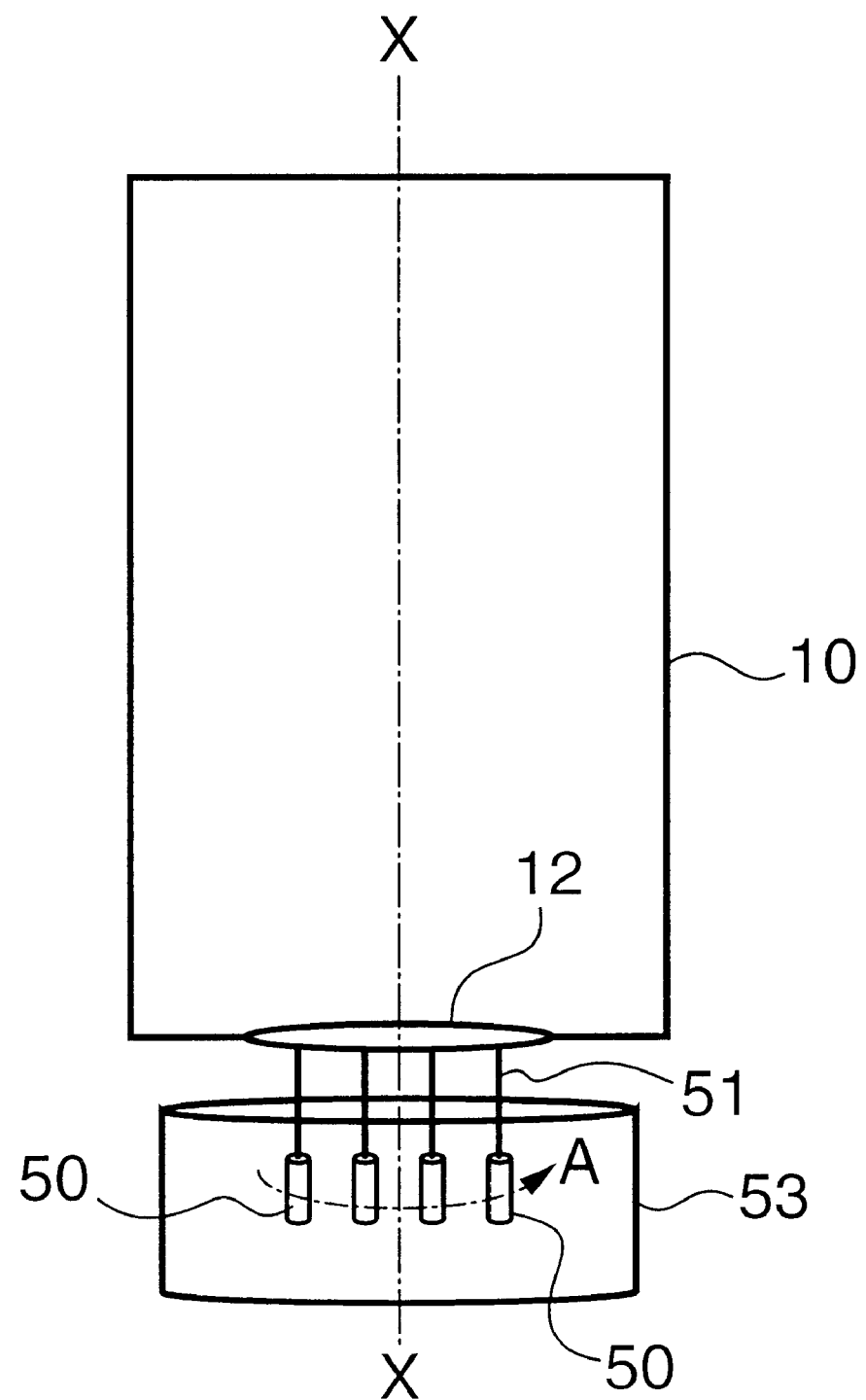
FIG. 7 is a schematic diagram of an vestibular response evaluation apparatus with a damping mechanism.

It is also desirable to damp the motion rapidly after the initial sudden controlled acceleration since otherwise the rapid motion will make the subject tends feel. An effective method for achieving this result is shown in the embodiment of FIG. 7. The platform 14 on the frame 10 is fixed by rods 51 to an array of vertical cylinders 50 that are suspended in a damping liquid 54 of suitable viscosity, for example water, contained in tank 52 below the frame. Alternatively, the frame could be coupled by suitable mechanical coupling means to an array of such cylinders located separately from the frame 10 but arranged so as to rotate with the frame in the direction A about its longitudinal axis X—X.

This embodiment exploits a property of bodies moving through a fluid. Upon initial rotation, the liquid flow over the cylinders is laminar and the resistance to motion is very small. When the liquid flow becomes turbulent, there is a sudden and dramatic increase in resistance. This effect acts as an effective damping mechanism that permits the initial sudden acceleration sufficient to take the desired measurements, but ensures that the frame comes to a rapid stop as quickly as possible but without causing unnecessary discomfort to the subject.

The invention can be employed in the effective clinical diagnosis of dizziness and balance disturbances. This involves taking a careful history, performing an appropriate physical examination, testing vestibular function and hearing and sometimes using brain imaging. An effective vestibular test can help to localize an abnormality. For example, a significant change in the eye movement response to sudden rotation with all other tests normal would suggest a peripheral vestibular disturbance. Recording sudden episodes of saccadic eye movements when the head is placed in certain orientations would be virtually diagnostic of benign positional vertigo. Multiple test abnormalities would suggest a problem lying deeper within the central nervous system.

The present invention is not intended to replace the classical, clinical approach, but it does permit the improvement in sensitivity and reliability of the basic vestibular function test battery and thus enhances the ability to diagnose specifically vestibular abnormalities. This can be accomplished for less money than prior art techniques, making the method more widely affordable.

It will thus be appreciated that the present invention provides a diagnostics system for vestibular testing wherein a controlled sudden angular rotation about a longitudinal axis produces a significant subject vestibulo-ocular reflex response in a subject supported in the standing position. This invention also provides an effective means of EOG recording during high-yaw acceleration stimulation.

The application of the stimulus is applied while the subject is in the erect, and preferably vertical, position greatly decreases the inertia of the overall system. The decreased inertia allows for simple stimulus delivery systems such as a mechanical, stored energy system, with computerized feedback.

The fastening of the EOG electrode leads via a central stabilizing ring and adjustable electrode connectors improves the quality of recordings by minimizing motion artifacts caused by mechanical stress on the electrodes. The design of the head adapter provides improved coupling between the stimulus transducers and the head while allowing for the presence of electrodes.

The use of three mutually perpendicular angular velocity transducers renders the head velocity measurement immune to sensor alignment issues.

The method is affordable due to the use of simple mechanical means for delivering the stimulus and automating the diagnostics. This removes the need for high-powered turntables and highly trained technicians and support personnel.

The method of the invention can substantially eliminate any potential inputs from compensatory mechanisms, such as cervicoocular reflex, by rotating the whole subject, from compensatory mechanisms, such as visual tracking or a contralateral vestibular reference, by looking at only the very early reaction to a high-acceleration stimulus thereby restricting the response to only its pure reflex component, and from compensatory mechanisms, such as efference copy, by only using externally applied passive rotations.

We claim:

1. A method of evaluating the vestibular function in a human subject, comprising:

constraining the human subject in a substantially erect position so that the head moves in unison with the rest of the body;

imparting a controlled stimulus in the form of a sudden angular acceleration to the body, and;

measuring the subject's ocular response to the controlled stimulus.

2. A method as claimed in claim 1, wherein the subject's ocular response is measured by electro-oculography.

3. A method as claimed in claim 1, wherein the human subject is rotated about its longitudinal axis.

4. A method as claimed in claim 3, wherein the subject is disposed in a substantially vertical position.

5. A method as claimed in claim 3, wherein the subject is disposed in a substantially horizontal position.

6. A method as claimed in claim 3, wherein the subject is disposed in an erect inclined position.

7. A method as claimed in claim 1, wherein the angular velocity of the subject is measured as a whole and compared with the ocular response to evaluate the vestibular function.

8. A method as claimed in claim 7, wherein the angular velocity is measured in three orthogonal directions.

9. A method as claimed in claim 7, wherein the ocular response is subjected to signal processing to extract eye velocity.

10. A method as claimed in claim 9, wherein said signal processing comprises filtering and differentiation.

11. A method as claimed in claimed in claim 9, wherein the eye velocity is compared with the angular velocity of the subject to evaluate the vestibular function.

12. A method as claimed in claim 11, wherein the eye velocity and head velocity are also compared with standard data in evaluating the vestibular function.

13. A method as claimed in claim 1, wherein the subject is rapidly brought to rest with the aid of a fluid damping mechanism.

14. A method as claimed in claim 13, wherein the fluid damping mechanism comprises one or more bodies coupled to rotate with the subject and suspended in a damping fluid.

15. A method as claimed in claim 14, wherein the damping fluid is water.

16. An apparatus for evaluating vestibular function in a human subject, comprising:

a frame for supporting the human subject in a substantially erect position with the head constrained so that it moves in unison with the rest of the body, the frame being rotatable about a longitudinal axis of the subject;

an arrangement for measuring ocular response to a controlled stimulus in the form of a sudden angular acceleration imparted to the frame, at least one sensor for measuring the angular velocity of the subject's head; and a processing unit for deriving the vestibular function from the subject's ocular response and the angular velocity.

17. An apparatus as claimed in claim 16, wherein the frame is mounted for rotation about a vertical axis.

18. An apparatus as claimed in claim 16, wherein the frame is mounted for rotation about a horizontal axis.

19. An apparatus as claimed in claim 18, wherein the frame is mounted for rotation about a vertical axis.

20. An apparatus as claim in claim 17, wherein the frame has a first clamp for constraining the subject's body and a second clamp for constraining the subject's head.

21. An apparatus as claimed in claim 16, wherein said arrangement includes ocular electrodes attached to electrode leads that are fastened with the aid of a stabilizing ring attached to the subject's head.

22. An apparatus as claimed in claim 16, wherein said at least one sensor for measuring angular velocity comprises three mutually perpendicular angular velocity sensors.

23. An apparatus as claimed in claim 16, wherein said arrangement for measuring ocular response is an electro-oculogram unit.

24. An apparatus as claimed in claim 23, wherein said processing unit is arranged to process an output of said electro-oculogram unit to derive eye velocity therefrom.

25. An apparatus as claimed in claim 24, wherein said processing unit is programmed to compare said eye velocity with head velocity to evaluate the vestibular function.

26. An apparatus as claimed in claim 25, wherein said processing unit is further programmed to compare said eye velocity and head velocity with standard data in order to evaluate the vestibular function.

27. An apparatus as claimed in claim 16, further comprising a mechanical energy storage device, and an impulse unit for imparting a sudden acceleration to said frame.

28. An apparatus as claimed in claim 16, further comprising a headgear on which said at least one angular velocity sensor is mounted to measure directly said angular velocity of the subject's head without slip.

29. An apparatus in claim 16, wherein the frame is coupled to a fluid damping mechanism for rapidly bringing the subject to rest after the initial acceleration.

30. An apparatus as claimed in claim 29, wherein said fluid damping mechanism comprises one or more bodies coupled to rotate with the subject and suspended in a damping fluid.

31. An apparatus as claimed in claim 30, wherein an array of said bodies is arranged to rotate about a central axis.

32. An apparatus as claimed in claim 31, wherein said bodies are cylindrical.

* * * * *